United States Patent [19]

Noda

[11] Patent Number: 5,747,584
[45] Date of Patent: May 5, 1998

[54] NONWOVEN MATERIALS COMPRISING BIODEGRADABLE COPOLYMERS

[75] Inventor: Isao Noda, Cincinnati, Ohio

[73] Assignee: The Procter & Gamble Company, Cincinnati, Ohio

[21] Appl. No.: 799,850

[22] Filed: Feb. 13, 1997

Related U.S. Application Data

[60] Division of Ser. No. 608,233, Feb. 28, 1996, Pat. No. 5,685,756, which is a continuation-in-part of Ser. No. 465,046, Jun. 6, 1995, Pat. No. 5,618,855, Ser. No. 422,008, Apr. 13, 1995, Pat. No. 5,498,692, and Ser. No. 188,271, Jan. 28, 1994, abandoned, and a continuation of Ser. No. 472,353, Jun. 6, 1995, Pat. No. 5,502,116, and a continuation-in-part of Ser. No. 447,136, Jun. 1, 1995, Pat. No. 5,648,452, which is a continuation of Ser. No. 341,808, Nov. 18, 1994, abandoned, which is a continuation-in-part of Ser. No. 189,015, Jan. 28, 1994, abandoned, said Ser. No. 465,046, is a continuation of Ser. No. 370,738, Jan. 12, 1995, abandoned, which is a continuation of Ser. No. 247,539, May 23, 1994, abandoned, which is a continuation of Ser. No. 187,969, Jan. 28, 1994, abandoned, said Ser. No. 422,008, is a continuation of Ser. No. 371,665, Jan. 12, 1995, abandoned, which is a continuation of Ser. No. 306,349, Sep. 15, 1994, abandoned, which is a continuation-in-part of Ser. No. 247,539, said Ser. No. 472,353, is a continuation of Ser. No. 422,011, Apr. 13, 1995, abandoned, which is a continuation of Ser. No. 371,940, Jan. 12, 1995, abandoned, which is a continuation of Ser. No. 189,029, Jan. 28, 1994, abandoned.

[51] Int. Cl.$^6$ ................... C08F 2/32; D04H 3/08
[52] U.S. Cl. ............... 524/801; 156/181; 156/332; 528/361
[58] Field of Search ............ 524/801; 528/361; 156/181, 332

[56] References Cited

U.S. PATENT DOCUMENTS

| | | | |
|---|---|---|---|
| 4,091,058 | 5/1978 | Sander et al. | 264/11 |
| 4,603,070 | 7/1986 | Steel et al. | 428/88 |
| 4,944,734 | 7/1990 | Wallach | 604/358 |
| 5,004,664 | 4/1991 | Fuller et al. | 430/106.6 |
| 5,053,482 | 10/1991 | Tietz | 528/272 |
| 5,191,016 | 3/1993 | Yalpani | 525/54.2 |
| 5,350,627 | 9/1994 | Nemphos et al. | 428/288 |

FOREIGN PATENT DOCUMENTS

| | | | |
|---|---|---|---|
| 0 540 182 A2 | 5/1993 | European Pat. Off. | C08L 67/04 |
| 0 540 182 A3 | 5/1993 | European Pat. Off. | C08L 67/04 |
| 40 40 158-A1 | 12/1990 | Germany | C09D 167/04 |
| 4-136066-A | 5/1992 | Japan | C08L 67/04 |
| 4-136067-A | 5/1992 | Japan | C08L 67/04 |
| 5-017590-A | 1/1993 | Japan | C08J 5/00 |
| 5-093317-A | 4/1993 | Japan | D01F 8/14 |
| 5-093318-A | 4/1993 | Japan | D01F 8/14 |
| 5-230351-A | 9/1993 | Japan | C08L 67/02 |
| 91/13207 | 9/1991 | WIPO | D21H 19/62 |
| 95/02649 | 7/1994 | WIPO | C09J 167/04 |
| 9502649 | 1/1995 | WIPO | |

OTHER PUBLICATIONS

Barnard, G.N. & J.K.M. Sanders, (Feb. 25, 1989) "The Poly-β-hydroxybutyrate Granule in Vivo", The Journal of Biological Chemistry 264(6) 3286-3291.

Berger, E., B.A. Ramsay, J.A. Ramsay, C. Chavarie, and G. Braunegg, (Jul./Aug. 1989) "PHB Recovery by Hypochlorite Digestion of Non-PHB Biomass", Biotechnology Techniques 3(4) 227-232.

Dave, P., R.A. Gross, C. Burcato, S. Wong & S.P. McCarthy, (Apr. 23, 1990) "Biodegradation of Blends Containing Poly(3-hydroxybutyrate-co-valerate)", Polymeric Materials Science and Engineering 62 231-235.

Drelich, A., "Thermal Bonding With Fusible Fibers", (Sep. 1985) Nonwovens Industry 12-26.

Dunlop, W.F. & A.W. Robards, (Jun. 1973) "Ultrastructural Study of Poly-β-hydroxybutyrate Granules from *Bacillus cereus*", J. Bacteriol. 114(3) 1271-1280.

Ellar, D., D.G. Lundgren, K. Okamura & R.H. Marchessault, (Aug. 14, 1968) "Morphology of Poly-β-hydroxybutyrate Granules", J. Mol. Biol. 35(3) 489-502.

Horowitz, D.M., J. Clauss, B.K. Hunter & J.K.M. Sanders, (May 6, 1993) "Amorphous Polymer Granules", Nature 363 23.

Lauzier, C.A., C.J. Monasterios, I. Saracovan, R.H. Marchessault & B.A. Ramsay, (May 1993) "Film Formation and Paper Coating with Poly(β-hydroxyalkanoate), a Biodegradable Latex", Tappi Journal 76(5) 71-77.

Lenz, R.W., (Sep. 1989) "Stereoregular Poly-β-hydroxyalkanoates Produced by Bacteria or Prepared from β-lactones", Polym Prepr. (ACS Div. Polym. Chem.) 30(2) 416-417.

Marchessault, R.H. & C.J. Monasterios, (Apr. 23, 1990) "Influence of Copolymer Structure on Properties of Poly-β-Hydroxyalkanoates", Polymeric Materials Science Engineering 62 226-230.

Marchessault, R.H., P. Rioux and I. Saracovan (Apr. 1993), "Direct Electrostatic Coating of Paper", Nordic Pulp and Paper Research Journal-1 211-216.

Marchessault, R.H., C.J. Monasterios & P. Lepoutre, (1990) "Properties of Poly-β-hydroxyalkanoate Latex: Nascent Morphology, Film Formation and Surface Chemistry", Novel Biodegradable Microbial Polymers (E.A. Dawes, ed.), Kluwer Academic Publishers 97-112.

Ramsay, B.A., I. Saracovan, J.A. Ramsay & R.H. Marchessault, (Mar. 1991), "Continuous Production of Long-Side-Chain Poly-β-Hydroxyalkanoates by *Pseudomonas oleovorans*", Applied and Environmental Microbiology 57(3) 625-629.

*Primary Examiner*—Morton Foelak
*Attorney, Agent, or Firm*—Bart S. Hersko; David L. Suter; Jacobus C. Rasser

[57] ABSTRACT

This invention relates to a nonwoven material comprising an adhesive comprising polyhydroxyalkanoate (PHA). This invention also relates to an absorbent article comprising such nonwoven material. This invention also relates to a composition comprising PHA and a surfactant. This invention relates to a method for preparing the nonwoven material.

7 Claims, No Drawings

NONWOVEN MATERIALS COMPRISING BIODEGRADABLE COPOLYMERS

This is a division of application Ser. No. 08/608,233, filed on Feb. 28, 1996, now U.S. Pat. No. 5,685,756 which is a continuation-in-part of application Ser. No. 08/465,046, filed Jun. 6, 1995, now U.S. Pat. No. 5,618,855, which is a continuation of application Ser. No. 08/370,738, filed Jan. 12, 1995, now abandoned, which is a continuation of application Ser. No. 08/247,539, filed May 23, 1994, now abandoned, which is a continuation of application Ser. No. 08/187,969 filed Jan. 28, 1994, now abandoned; and a continuaion-in-part of application Ser. No. 08/422,008, filed Apr. 13, 1995, now U.S. Pat. No. 5,498,692, which is a continuation of application Ser. No. 08/371,665, filed Jan. 12, 1995, now abandoned, which is a continuation of application Ser. No. 08/306,349, filed Sep. 15, 1994, now abandoned, which is a continuation-in-part of application Ser. No. 08/247,539, filed May 23, 1994, now abandoned, which is a continuation of application Ser. No. 08/187,969, filed Jan. 28, 1994, now abandoned; and a continuation-in-part of application Ser. No. 08/188,271, filed Jan. 28, 1994, now abandoned; and a continuation of application Ser. No. 08/472,353, filed Jun. 6, 1995, now U.S. Pat. No. 5,502,116 which is a continuation of application Ser. No. 08/422,011, filed Apr. 13, 1995, now abandoned, which is a continuation of application Ser. No. 08/371,940, filed Jan. 12, 1995, now abandoned, which is a continuation of application Ser. No. 08/189,029, filed Jan. 28, 1994, now abandonded; and a continuation-in-part of application Ser. No. 08/447,136, now U.S. Pat. No. 5,648,452 filed Jun. 1, 1995, which is a continuation of application Ser. No. 08/341,808, filed Nov. 18, 1994, now abandoned, which is a continuation-in-part of application Ser. No. 08/189,015, filed on Jan. 28, 1994, now abandoned.

TECHNICAL FIELD

This invention relates to nonwoven materials and adhesives therefor, comprising biodegradable copolymers.

BACKGROUND

Polymers find uses in a variety of plastic articles including films, sheets, fibers, foams, molded articles, adhesives, nonwoven materials and many other specialty products which usually have a short use cycle. The majority of these products end up in the solid waste stream, headed for limited and increasingly expensive landfill space. While recycling has sought to address this problem, the nature of polymers and polymer products limits the number of possible recycling applications. Repeated processing of polymers and polymer products results in degradation of material and consequently poor mechanical properties. For example, different grades of chemically similar plastics (e.g., polyethylenes of different molecular weights, as used in milk jugs and grocery sacks) mixed upon collection can cause processing problems that make the reclaimed material inferior or unusable.

In absorbent article applications such as diapers, sanitary napkins, pantiliners and the like, the product contains several different types of plastics. In these cases, recycling is particularly costly because of the difficulty in separating the different components. Disposable products of this type generally comprise some sort of fluid-permeable topsheet material, an absorbent core, and a fluid-impermeable backsheet material. Typically, absorbent core materials comprising wood pulp fibers and the like are compostable. However, typical topsheet and backsheet materials prepared from woven, nonwoven, or porous formed-film polyethylene or polypropylene materials are noncompostable. Thus there is a need to replace these noncomposatable materials with compostable material to provide disposable products which are compostable. U.S. Pat. No. 4,880,592, Martini et al., discloses a compostable film which, while cumbersome to prepare, is said to be suitable for diaper backsheet applications. An easily prepared, compostable nonwoven, suitable for a diaper topsheet, is desired for compostable product.

However, any new compostable materials and the articles and products prepared from them must possess certain mechanical properties to facilitate manufacture and consumer acceptance. For example, proper tensile strength, tensile modulus, tear strength, and the like are required for easily preparing the compostable article. The consumer requires properties such as impact strength, puncture strength, and moisture transmission, which influence the compostable article's durability.

Once the absorbent article is disposed of and enters a composting process, other properties become important. The disposable should undergo an initial breakup to much smaller particles during the initial stages of composting.

In the past, the biodegradability and physical properties of a variety of polyhydroxyalkanoates (PHAs) have been studied. PHAs are polyester compounds produced by a variety of microorganisms, such as bacteria and algae. While PHAs have been of general interest because of their biodegradable nature, their use as a plastic material has been hampered by their thermal instability. PHB degrades at temperatures near its melt temperature. Due to this thermal instability, commercial applications of PHB have been limited.

Based on the foregoing, there is a need for nonwoven materials and articles containing them that can biodegrade. To that end, there is a need for a nonwoven material whose fibers are bound together by an adhesive that can biodegrade. In effect, such biodegradable articles would facilitate the "recycling" of plastic articles into another usable product, topsoil, through composting.

OBJECTS OF THE INVENTION

It is an object of the present invention to provide a nonwoven material comprising an adhesive comprising a biodegradable polyhydroxyalkanoate (PHA).

It is also an object of the present invention to provide a biodegradable PHA as an adhesive for nonwoven materials.

It is also an object of the present invention to provide a composition comprising a biodegradable PHA useful as an adhesive for nonwoven materials.

It is also an object of the present invention to provide a disposable sanitary article comprising a nonwoven comprising an adhesive comprising a biodegradable PHA.

It is also an object of the present invention to provide a method of using a biodegradable PHA to make nonwoven materials.

SUMMARY

This invention relates to biodegradable PHA copolymers as adhesives useful in preparing nonwovens, and the nonwovens made from them.

The adhesive comprises a PHA of least two different randomly repeating monomer units wherein each randomly repeating monomer unit has the structure:

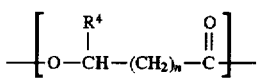

wherein each $R^4$ is chosen from H, or any of $C_1$ to about $C_{19}$ alkyl or $C_1$ to about $C_{19}$ alkenyl and each n is from 1 to about 4.

Preferably, this invention further relates to adhesives useful in preparing nonwovens, and the nonwovens made therefrom, wherein the copolymer comprises at least two randomly repeating monomer units wherein the first monomer unit has the structure;

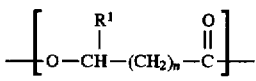

wherein $R^1$ is H, or $C_1$ to about $C_{19}$ alkyl or $C_1$ to about $C_{19}$ alkenyl, and n is independently 1 or 2; the second monomer unit has the structure:

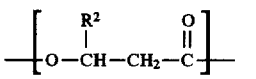

wherein $R^2$ is $C_3$ to about $C_{19}$ alkyl or $C_1$ to $C_{19}$ alkenyl; and wherein at least 50% of the random repeating monomer units have the structure of the first monomer unit.

More preferably, the first monomer unit has the above structure, wherein $R^1$ is H, $C_1$, or $C_2$ alkyl and n is 1 or 2.

This invention further relates to nonwoven materials and articles comprising them comprising a biodegradable copolymer as an adhesive.

DETAILED DESCRIPTION

This invention provides a biodegradable nonwoven employing a compostable adhesive as a binder, and disposable articles containing these nonwovens which are easily processed into the article and posses increased biodegradability and/or compostability.

As used herein, "alkyl" means a saturated carbon-containing chain which may be straight or branched; and substituted (mono- or poly-) or unsubstituted. "Substituted," when applied to any radical, refers to any art recognized substitution. Examples of these substitutions are known in the art and can be found in and prepared using, for example, March, *Advanced Organic Chemistry*, 3rd Ed. (Wiley-Interscience), hereby incorporated by reference, and other similar sources.

As used herein, "unsaturated" means alkyl containing one or more double bonds.

As used herein, "alkenyl" means a carbon-containing chain which may be monounsaturated (i.e., one double bond in the chain) or polyunsaturated (i.e., two or more double bonds in the chain); straight or branched; and substituted (mono- or poly-) or unsubstituted.

As used herein, "PHA" means a polyhydroxyalkanoate, as described throughout the specification.

As used herein, "PHB" means the homopolymer poly-3-hydroxybutyrate.

As used herein, "PHBV" means the copolymer poly(3-hydroxybutyrate-co-3-hydroxyvalerate). This copolymer is also known as PHB-PHV and BIOPOL.

As used herein, "biodegradable" means the ability of a compound to ultimately be degraded completely by microorganisms and/or natural environmental factors.

As used herein, "compostable" means a material that meets the following three requirements:

(1) the material is capable of being processed in a composting facility for solid waste;

(2) if so processed, the material will end up in the final compost; and (3) if the compost is used in the soil, the material will ultimately biodegrade in the soil.

For example, a polymer material present in solid waste submitted to a composting facility for processing does not necessarily end up in the final compost. Certain composting facilities subject the solid waste stream to air classification prior to further processing, in order to separate paper and other materials. A polymer would most probably be separated from the solid waste stream in such an air classification and therefore not be processed in the composting facility. Nevertheless, it may still be a "compostable" material according to the above definition because it is "capable" of being processed in a composting facility.

The requirement that the material ends up in the final compost typically means that it undergoes a form of degradation in the composting process. Typically, the solid waste stream is subjected to shredding. Here the nonwoven appears in the final compost regardless of composition, biodegradable or not. Therefore, meeting requirement (2) is not enough for a material to be compostable within the present definition.

The compostable material differs from material like polyethylene in that, (3) the material ultimately will biodegrade in the soil. This biodegradability requirement does not require the composting process or the use of composting soil. Nor is it necessary that biodegradation be rapid. Provided that the nonwoven and its decomposition products are non-toxic or polluting, their biodegradation may take months or years.

All copolymer composition ratios recited herein refer to mole ratios, unless specifically indicated otherwise.

As used herein, "plastic article" means a copolymer processed into a film, sheet, fiber, foam, molded article, nonwoven material, elastomer, adhesive, or consumer good, preferably a nonwoven material or consumer good comprising a nonwoven material. A "disposable plastic article" or "disposable article" refers to these articles, when they are likely to be disposable, whether or not they were intended as such. Preferred articles employ the nonwovens of the invention.

As used herein "adhesive" means a material that joins two other materials, called adherents, together. These adherents can be sheets, fibers and the like. Preferably the adherent is a fiber, thus the adhesive binds the fibers together into a nonwoven material.

As used herein the term "nonwoven" means, textile-like material, usually in flat sheet form, comprising fibers assembled in webs that are manufactured by processes other than spinning, weaving or knitting. Such material may be porous or non porous. "Textile like" refers to material used in the manufacture of textiles as well as material made to perform in a manner similar to textiles, without being woven, spun or knitted into textiles. Nonwoven materials include nonwoven fabrics, bonded fabrics, formed fabrics, engineered fabrics, paper-like materials and the like. Nonwoven materials are useful, for example, as topsheets or backsheets for disposable sanitary articles and the like.

As used herein a "disposable sanitary article" includes any object made from the materials described herein that is worn on the body for hygienic or medical purposes. Thus disposable sanitary articles include catamenial products, incontinence products, bandages, wound dressings, surgical pads and the like.

The PHAs disclosed herein are useful as adhesives in nonwovens.

PHAs useful in the present invention comprise at least two randomly repeating monomer units wherein each randomly repeating monomer unit has the structure:

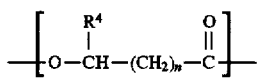

wherein each $R^4$ is chosen from H, or any of $C_1$ to about $C_{19}$ alkyl or $C_1$ to about $C_{19}$ alkenyl and each n is 1 to about 4.

Preferably PHAs useful in the present invention comprise at least two randomly repeating monomer units wherein the first monomer unit has the structure:

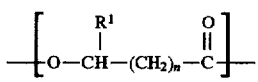

wherein $R^1$ is H, or $C_1$ to about $C_{19}$ alkyl or $C_1$ to about $C_{19}$ alkenyl, and n is independently 1 or 2; the second monomer unit has the structure:

wherein $R^2$ is about $C_3$ to about $C_{19}$ alkyl or $C_3$ to about $C_{19}$ alkenyl; and wherein at least 50% of the random repeating monomer units have the structure of the first monomer unit.

In a preferred embodiment, the first monomer unit has the above structure, wherein $R^1$ is H, $C_1$ or $C_2$ alkyl and n is 1 or 2.

A description of the synthesis of PHAs useful in the present invention and their properties, such as crystallinity, melt temperature and the like, as well as a description of products made using these PHAs is found in copending U.S. patent application Ser. No. 08/370,738, filed Jan. 12, 1995, incorporated herein by reference. Specifically this application describes PHAs having two randomly repeating monomer units wherein the first randomly repeating monomer unit has the structure

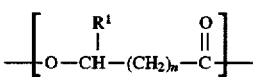

wherein $R^1$ is H, or $C_1$ or $C_2$ alkyl, and n is 1 or 2; the second randomly repeating monomer unit has the structure

wherein $R^2$ is a $C_3$ to about $C_{19}$ alkyl or $C_3$ to about $C_{19}$ alkenyl; and wherein at least 50% of the randomly repeating monomer units have the structure of the first randomly repeating monomer unit.

Additional PHAs useful in the present invention include those set forth in U.S. patent application Ser. No. 08/188,271, filed Jan. 28, 1994, incorporated herein by reference. Specifically this application describes PHAs having two randomly repeating monomer units; the first randomly repeating monomer unit having the structure

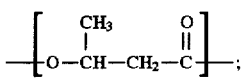

the second randomly repeating monomer unit having the structure

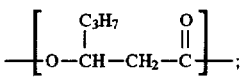

and wherein at least 50% of the randomly repeating monomer units have the structure of the first randomly repeating monomer unit.

Additional PHAs useful in the present invention include those set forth in U.S. patent application Ser. No. 08/422,011, filed Apr. 13, 1995, incorporated herein by reference. Specifically this application describes PHAs having two randomly repeating monomer units; the first randomly repeating monomer unit having the structure

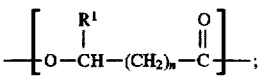

wherein $R^1$ is H or $C_2$ alkyl, and n is 1 or 2; the second randomly repeating monomer unit having the structure

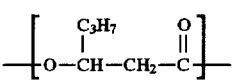

and wherein at least 50% of the randomly repeating monomer units have the structure of the first randomly repeating monomer unit. Related disclosure of these PHAs is found in U.S. patent application Ser. No. 08/188,271, filed Jan. 28, 1994, U.S. patent application Ser. No. 08/422,011, filed Apr. 13, 1995, U.S. patent application Ser. No. 08/203,260, filed Feb. 28, 1994, which describe a nonwoven comprising PHA, and method of making it, and U.S. patent application Ser. No. 08/203,289, filed Feb. 28, 1994, which describes a nonwoven comprising PHA, and method of making it.

The structures of the polymers contained in these references are all within the scope of the structure described in the summary and in the claims.

In one embodiment of the present invention, at least about 50%, but less than 100%, of the randomly repeating monomer units (RRMUs) have the structure of the first RRMU; more preferably at least about 60%; more preferably at least about 70%; more preferably at least about 80%; more preferably still at least about 90%.

Preferred RRMUs of this embodiment include the following:

| $R^1$ | n | Repeating Unit Name |
|---|---|---|
| Methyl | 1 | 3-hydroxybutyrate |
| Ethyl | 1 | 3-hydroxyvalerate |
| H | 2 | 4-hydroxybutyrate |
| H | 4 | 6-hydroxycaproate |
| Methayl | 4 | 6-hydroxycaprylate |
| H | 3 | 5-hydroxyvalerate |
| Methyl | 3 | 5-hydroxycaproate |

The preceding list of RRMUs for any embodiment is not exhaustive. Certainly other RRMUs are envisioned, all of which are embraced by the claims. Variations of these will be immediately apparent to the skilled artisan.

In another embodiment, the copolymer useful in the present invention comprises one or more additional RRMUs having the structure

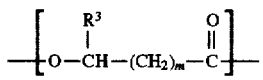

wherein $R^3$ is H, or $C_1$ to about $C_{19}$ alkyl or $C_1$ to about $C_{19}$ alkenyl; and m is 1 or 2; and wherein the additional RRMUs are not the same as the first RRMU or the second RRMU. Preferably the copolymer comprises 3 to about 20 or more different RRMUs.

In a preferred embodiment of the present invention, $R^3$ is a $C_1$ to about $C_{19}$ alkyl or alkenyl; and m is 1.

Preferred RRMUs of this embodiment include the following:

| $R^3$ | n | Repeating Unit Name |
|---|---|---|
| Methyl | 1 | 3-hydroxybutyrate |
| Ethyl | 1 | 3-hydroxyvalerate |
| H | 2 | 4-hydroxybutyrate |
| H | 1 | 6-hydroxypropionate |

The preceding list of RRMUs for any embodiment is not exhaustive. Certainly other RRMUs are envisioned, all of which are embraced by the claims. Variations of these will be immediately apparent to the skilled artisan.

Preferably, the PHAs used in the present invention comprising two RRMUs have a first RRMU having the structure

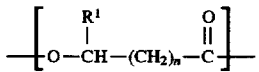

wherein $R^1$ is H, or $C_1$ or $C_2$ alkyl, and n is 1 or 2; and a second RRMU having the structure

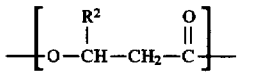

wherein when $R^1$ is $C_1$ or $C_2$ and n is 1, $R^2$ is a $C_{12}$ to about $C_{19}$ alkyl or alkenyl; when $R^1$ is $C_1$ or $C_2$ and n is 2, $R^2$ is a $C_3$ to about $C_{19}$ alkyl or alkenyl; and when $R^1$ is H and n is 1 or 2, $R^2$ a $C_3$ to about $C_{19}$ alkyl or alkenyl; and wherein at least 50% of the RRMUs have the structure of the first RRMU. More preferably $R^2$ is an alkyl.

Yet more preferably, novel biodegradable PHAs of the present invention comprising three RRMUs, have a first RRMU having the structure

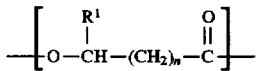

wherein $R^1$ is H, or $C_1$ or $C_2$ alkyl or $C_1$ or $C_2$ alkenyl, and n is independently 1 or 2; a second RRMU having the structure

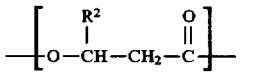

wherein $R^2$ is a $C_3$ to about $C_{19}$ alkyl or $C_3$ to about $C_{19}$ alkenyl; and a third RRMU having the structure

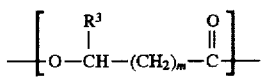

wherein $R^3$ is H, or a $C_1$ to about $C_{19}$ alkyl or $C_3$ to about $C_{19}$ alkenyl; and m is 1 or 2; wherein at least 50% of the RRMUs have the structure of the first RRMU; and wherein the third RRMU is not the same as the first RRMU or the second RRMU.

Synthesis of biodegradable PHAs, and attendant considerations such as crystallinity, melt temperature and the like are described in U.S. patent application Ser. No. 08/465,046, filed Jun. 6, 1995, U.S. patent application Ser. No. 08/422, 009, filed Apr. 13, 1995, U.S. patent application Ser. No. 08/422,008, filed Apr. 13, 1995, U.S. patent application Ser. No. 08/188,271, filed Jan. 28, 1994, U.S. patent application Ser. No. 08/422,011, filed Apr. 13, 1995, U.S. patent application Ser. No. 08/203,260, filed Feb. 28, 1994 and U.S. patent application Ser. No. 08/203,289, filed Feb. 28, 1994, all incorporated herein by reference; hereinafter collectively referred to as the "Parent Applications").

The PHAs of the present invention can be processed into a variety of plastic articles, including but not limited to, films, sheets, fibers, foams, molded articles, nonwoven materials, elastomers, and adhesives. Disclosure related to the preparation of such articles is found in the Parent Applications. Of particular interest in this application is the use of PHAs in nonwoven materials preferably their use as adhesives (e.g., binders) in making those nonwoven materials.

Nonwoven Materials and Adhesives Comprising PHA

A. Nonwovens

A general overview of nonwoven materials can be found in the ENCYCLOPEDIA OF POLYMER SCIENCE AND ENGINEERING, Second Edition, Vol. 10, pp. 204–226 (referred to hereafter as "EPSE-4"). The thickness of the nonwoven sheets may vary from 25 μm to several centimeters, and the weight from 10 g/m² to 1 kg/m².

In contrast to conventional textiles, the fundamental structure of all nonwovens is a web of fibers arranged more or less randomly (NONWOVENS IND., Vol. 17, p. 36 (March 1986), NONWOVENS WORLD, Vol. 1, p. 36 (May-Jun. 1986)). Nonwoven materials have a wide range of physical properties depending on the material and process used in forming the fiber web foundation of the nonwoven. This material may be self-supporting and stiff like paper or drapable like a conventional cloth. Tensile, tear, and tactile properties in the nonwoven arise from the fiber and adhesive or other chemical and physical bonding, fiber-to-fiber friction created by entanglement, and reinforcement by other materials such as foams and films (see EPSE-4).

1. Method of Manufacture of Nonwoven Materials

The nonwoven materials of the present invention may be made by conventional techniques known in the art. Typically the production of nonwoven materials involves: 1) making fibers of various lengths and diameters; 2) creating a web of these fibers; and 3) bonding of fibers within the web by adhesive (sometimes called a binder), or by mechanical-frictional forces created by fiber contact or entanglement, although this process need not necessarily take place in this order. In addition to these steps, reinforcing the web by forming a composite with other materials (e.g., yarns, scrims, films, nettings, and unbonded webs) is sometimes preferred. Variations of one or several of these steps or their order allows for the enormous range of processes and of nonwoven fiber types.

The term "staple fibers" was originally applied to fibers of natural origin long enough to be processed on textile machinery, but excluding endless filaments, e.g., silk. In the present context, "staple fibers" are of relatively uniform length, ca. 1.3–10.2 cm, with a regular crimp i.e., a three-dimensional wavelike shape. Regenerated and other extruded fibers which are endless as formed, are typically cut during the manufacturing process to meet a processing or market need or specification. Extruded fibers can also be produced as continuous filaments without crimp.

The processes for forming webs from staple fibers differ from those using continuous filaments. Nonwoven material obtained from staple and filament fiber webs may differ substantially in properties (see EPSE-4).

The mechanical properties of the fibers, as well as of the adhesives used to adhere the nonwoven fibers to each other influences the properties of the nonwoven (see EPSE-4).

Other fibrous materials that may be used in the nonwovens of the present invention in combination with the PHA are natural fibers such as silk, wool, linen and the like; cellulosics, such as wood pulp, paper fibers, cotton, cellulose and the like; regenerated fibers including viscose rayon and cellulose acetate and the like; and synthetic fibers like polyesters, such as poly(ethylene terephthalate) (PET), other PHAs and the like; the polyamides, such as nylon-6, nylon 6,6, and the like; polyalkylenes, such as polypropylene (PP), polyethylene (PE) and other synthetics such as poly(vinyl alcohol) and the like.

The choice of fiber depends upon the intended application. For example, facings of disposable diapers or sanitary napkins made from PHA nonwoven materials of the present invention preferably feel dry even when the absorbent, inner layer is saturated. Hence, a hydrophobic polymer, such as a polyester, polyamide, polyalkylene and the like, is preferred for use in these products.

For applications where water absorbency is desirable, hydrophilic fibers are preferred. For example, a cellulosic fiber or a polyvinyl alcohol fiber or the like would be preferred in making a nonwoven towelette.

For applications where fluid impermeability is desirable, the nonporous nonwoven preferably employ:

1) fibers which repel fluids;
2) a web dense enough to provide aviod holes or pores in the nonwoven;
3) enough adhesive to seals any holes or pores in the nonwoven web, Such nonporous nonwoven materials are useful for mailing envelopes, containers, vapor barriers, diaper backsheets and the like Other important fiber characteristics that affect performance include length, diameter, density, crimp, cross section shape, spin-finish (e.g., lubricant added to the surface of extruded fibers to enhance processability), delustering (e.g., small amounts of $TiO_2$ pigment added before extrusion to increase whiteness or to reduce sheen) and the draw ratio. These are all related to the fiber or the fiber web, and are discussed in EPSE-4.

These nonwovens can be made by several methods, for example the methods of Noda et al. exemplified in U.S. patent application Ser. Nos. 08/203,260, filed Feb. 28, 1994, and 08/203,289, filed Feb. 28, 1994, incorporated herein by reference, as well as art recognized methods.

a. Web-making methods

The characteristics of the fiber web influence the physical properties of the final product. These characteristics depend on fiber architecture, which is determined by the mode of web formation. Fiber architecture includes the predominant fiber direction, whether oriented or random, fiber shape (straight, hooked, or curled), the extent of interfiber engagement or entanglement, crimp, and compaction (web-density control). Web characteristics are also influenced by fiber diameter, length, web weight, and chemical and mechanical properties of the fiber material (see EPSE-4).

The choice of method for forming the web is determined primarily by fiber length. Initially, the methods for forming webs from staple-length fibers (fibers long enough to be handled by conventional spinning equipment, usually from about 1.2 to about 20 cm long, but not endless) are based -on the textile-carding process, whereas web formation from short fibers is based on papermaking technologies. Although these technologies are still in use, other methods have been subsequently developed. For example, webs are formed from long, virtually endless filaments directly from bulk polymer; both web and fibers are produced simultaneously (see EPSE-4). A variety of web-making methods are known, including carding, air-laying, wet-forming, spunbonding, and meltblowing.

Carding separates clumps of staple fibers mechanically into individual fibers and formed into a coherent web by the mechanical action of moving beds of closely spaced needles.

Air-laying improves orienting of fibers by capturing fibers on a screen from an airstream (see U.S. Pat. No. 3,338,992, G. A. Kinney, assigned to E. I. du Pont de Nemours & Co., Inc., issued Aug. 29, 1967). The fibers are separated by teeth or needles and introduced into an airstream.

Wet-forming typically employs very short fibers. Initially, webs are formed from short fibers by modified papermaking techniques. The fibers are continuously dispersed in a large volume of water or solvent and caught on a moving endless wire screen. Once the web is caught on the screen, it is transferred to belts or felts and dried on heated drums (see EPSE-4).

Spunbonding involves making fibers and web simultaneously, directly from bulk polymer. The bulk polymer is melted, extruded, and drawn into virtually endless filaments that are randomized and deposited onto belts as a continuous web. This process produces webs of low crimp filaments in the normal diameter range of about 1.7 dtex (1.5 den) or slightly higher. The birefringence and uniformity of diameter of these filaments are similar to standard textile fibers and filaments (see EPSE-4 and U.S. Pat. No. 4,163, 305 (Aug. 7, 1979), V. Semjonow and J. Foedrowitz (to Hoechst AG)).

Meltblowing prepares webs directly from bulk polymers (see U.S. Pat. No. 3,322,607, S. L. Jung, assigned to E. I. duPont de Nemours & Co., Inc., May 30, 1967). For example, molten PHA forced through very fine holes in a special die into a high velocity airstream forms very fine, although irregular, filaments of indeterminate lengths. The filaments are formed into a web and bonded simultaneously (see EPSE-4). The web consists primarily of very fine filaments.

b. Web bonding

The bonding of fibers (i.e., the adhering of fibers to each other) gives the strength to the web and influences the nonwoven properties. Both adhesive and mechanical means are used in bonding. Mechanical bonding uses bonding of fibers by frictional forces. Bonding can also be achieved by chemical means, e.g., formation of covalent bonds between binder and fibers (see EPSE-4).

In a preferred method, this bonding is accomplished with a compostable material, more preferably a PHA, as an adhesive. Such a preferred method of bonding of fibers used in a nonwoven material is described herein below.

B. Adhesive

A general discussion on adhesives can be found in the Encyclopedia of Polymer Science and Engineering, Vol. 1, pp. 547–577, (hereafter referred to as "EPSE-6"). Generally an adhesive is applied as a liquid, preferably of a low viscosity. The adhesive wets the adherent surface and may flow into the crevices in the adherent surfaces. In many cases, the liquid form of the adhesive is obtained by heating the adhesive to the point that flow occurs, dissolving or dispersing the material in a solvent, or starting with liquid monomers or oligomers that polymerize or react after application. Usually, the adhesive then solidifies by cooling, solvent evaporation, reaction or the like to provide the necessary strength to resist shearing forces.

The PHAs of the present invention may be processed into a variety of adhesives, including but not limited to, hot melt, solution, dispersion and pressure sensitive adhesives.

The method of using these adhesives and the choice of adhesive will depend upon the properties sought, the material to which the adhesive is applied and the application intended. For example, in preparing a nonwoven material, one would consider the mechanical characteristics of the unbonded nonwoven and its desired end application.

1. Hot-melt Adhesives.

As used herein, "hot-melt adhesive" refers to a thermoplastic polymer or copolymer (e.g., a PHA) that is heated to obtain a liquid of flowable viscosity, and, after application, cooled to obtain a solid. Generally, the molecular weight of the adhesive is tailored to provide good rheology as a melt and sufficient strength as a solid to resist shearing forces experienced in the application. The PHAs of the present invention are thermoplastic, and thus are particularly useful as hot-melt adhesives. The primary feature of hot-melt adhesives is the ability of the thermoplastic material (PHA) to flow above a certain temperature, and to provide a strong bond at the normal use temperature. Upon cooling, the material hardens, either through passing through the glass transition temperature or the crystallization temperature. This hardening lends physical integrity to the bond.

2. Solutions and Dispersions.

The adhesives of this invention may be applied either as solutions or in the form of aqueous dispersions. When using a solution or dispersion, heating is preferred to expedite drying or "setting" of the adhesive. The dispersion solids can vary from 5 to 95%, preferably less than 50%.

As used herein, "dispersion" refers to adhesives which are prepared or dispersed as larger particles in some carrier fluid. In addition to their economic advantage, dispersions containing 40–50% solids offer lower viscosity than solutions, even if the solids are high molecular-weight polymers (EPSE-6). Adhesive dispersions of the present invention may be dispersed by high shear in the presence of surfactants to obtain waterborne formulations by procedures which are well known to those skilled in the art.

One preferred method of using the adhesive is to prepare a solution or dispersion of the PHA in toluene, ethyl acetate, acetone, halogenated solvents (e.g., chloroform, 1,2 dichloroethane and the like) or other suitable solvent. To this solution or dispersion it is preferred that a surfactant be added. Surfactants may increase wetting ability of the adhesive, as well as dispersion characteristics. Preferably the surfactant is an anionic surfactant, cationic surfactant, zwitterionic surfactant, nonionic surfactant, amphoteric surfactant or the like, preferably a cationic surfactant. Preferred surfactants are described in U.S. Pat. Nos. 4,835,211, Noda et al., issued May 30, 1989, and 4,785,030, Noda et al., issued Nov. 15, 1988, incorporated herein by reference.

A more preferred surfactant is a surfactant of formula X—Y—Z; wherein X is a cationic radical chosen from primary, secondary or tertiary amines and their cations, quaternary ammonium, sulfonium and phosphonium and the like; Y is a nonionic diradical having up to about 20 repeating monomer units of —($OCH_2CH_2$)—; and Z is an alkyl or alkenyl radical comprising of from about 8 to about 20 carbons which is branched or linear and substituted or unsubstituted.

In a preferred embodiment, this surfactant is present in about 0.5% to about 20% by weight; preferably about 1% to about 1 0% by weight; more preferably about 2% to about 5% by weight. Where a surfactant is used, water may be added to the solution or dispersion. Where water is added, it may be preferable to remove any solvent in the solution or dispersion. This provides an "environmentally friendly" adhesive.

3. Pressure-sensitive Adhesives.

These adhesives are discussed in detail in U.S. patent application Ser. No. 08/465,046, filed Jun. 6, 1995, incorporated herein by reference.

4. Use of adhesives as binders in nonwovens

PHAs can be used as adhesives or "binders" in nonwoven materials. For longer fiber nonwovens, it is preferred that the nonbonded material be formed and then coated using the art recognized "dip" coating process, wherein the nonwoven is run through a bath of adhesive in a dispersion or solution, preferably a colloidal dispersion in water. The adhesive then dries or sets and is optionally pressed to provide the bonded nonwoven.

For materials lacking the mechanical integrity to withstand dip coating, it is preferred that spray coating be used. Spray coating uses a sprayed adhesive, preferably a heated water dispersion of the adhesive, which then dries or cures and is optionally pressed to provide the bonded nonwoven.

For materials which are made from fibers that are too short to be spray coated, the fibers themselves can be coated in a bath and the nonwoven formed from these adhesive coated materials. In this case, the nonwoven material typically cannot be formed in the absence of binder. Spray coating would likely disperse the fibers. Consequently, coating the fibers in a bath is preferred, for example, in making paper like materials.

In a preferred embodiment of the present invention, the adhesive is dispersed in an aqueous medium with the aid of a surfactant. Preferably, the surfactant will promote the spontaneous deposition of the adhesive to fibers. In a more preferred embodiment, the surfactant is of formula X—Y—Z; wherein X is a cationic radical chosen from primary, secondary or tertiary amines and their cations, quaternary ammonium, sulfonium and phosphonium and the like; Y is a nonionic diradical having up to about 20 repeating monomer units of —($OCH_2CH_2$)—, preferably 5 to about 20, more preferably about 10 to about 20; and Z is an alkyl or alkenyl radical comprising of from about 8 to about 20 carbons which is saturated or unsaturated, branched or linear, preferably saturated or monounsaturated, and of from about 15 to about 20 carbons.

Disposable Personal Care Products

The nonwovens described above are useful in many disposable products: For example, disposable sanitary articles comprising a liquid pervious topsheet comprising the nonwoven comprising the PHA of the invention, a liquid impervious backsheet, and an absorbent core positioned between the topsheet and backsheet. Such articles include infant diapers, adult incontinent briefs and pads, and feminine hygiene pads, liners and the like.

Additional personal care products comprising a PHA of the present invention include personal cleansing wipes; disposable health care products such as bandages, wound dressings, wound cleansing pads, surgical gowns, surgical covers, surgical pads; other institutional and health care disposables such as gowns, wipes, pads, bedding items such as sheets, pillowcases, and foam mattress pads.

Additional absorbent articles include paper products, such as towelettes, tissues, paper towels, disposable washcloths and the like: personal care products, such as sanitary napkins, diapers, incontinence briefs and the like; health care products, such as wound dressings, bandages, and the like. Many other absorbent articles are known in the art and are contemplated.

Importantly, the absorbent articles of this invention are biodegradable and/or compostable to a greater extent than conventional absorbent articles which employ standard materials, such as polyolefins, and the like.

The following examples are not intended to limit or define the invention in any way. The following nonlimiting examples merely illustrate the invention and teach the skilled artisan how to make and use the invention. Of course, it is obvious to the skilled artisan that variation of these examples, including any permutation claimed in this application can be prepared by the skilled artisan in light of the examples following.

Additional examples of preparation of PHAs used herein below, as well as further disclosure and examples of the manufacture of these articles and examples thereof, including the preparation of films, sheets, fibers, foams, molded articles and elastomers are described in the Parent Applications.

EXAMPLE 1

Compostable Nonwoven Fabric

Poly(3-hydroxybutyrate-co-3-hydroxyoctanoate) (PHB-O) at 2 mole % octanoate/98 mole % butyrate is introduced into a single screw extruder (Rheomix Model 202, Paramus, N.J.) with screw diameter of 0.75 inch. A constant taper screw having 20:1 length to diameter ratio and a 3:1 compression ratio is employed. The temperature of both heating zones of the extruder barrel is 25° C. above the melt temperature of the PHB-O. The extruder is equipped with a nozzle die containing 5 orifices of diameter 500 mm. The die is maintained at 20° C. above the melt temperature of the PHB-O. The polymer is melted within the extruder and pumped to the die at the other end of the extruder. The screw rpm is kept constant at 30 rpm. The polymer is forced through the die and the melted extruded fibers are lead through a region where a rapid air stream is applied such that the polymer fibers elongates and thins to approximately one fifth of the diameter of the orifices (ca. 100 μm). The fibers are collected on a cardboard mat. The mat is moved in a fashion so that a 10 cm×10 cm area is covered uniformly with fibers. Collection of fibers on the mat continues, until there is approximately 0.5 cm thick fiber mat. A wide distribution of fiber lengths are obtained up several inches in length. Most fiber lengths (over 50%) are in the range of 0.5 to 6 inches. The mat is then transferred to a Carver Press (Fred S. Carver Inc., Menomonee Falls, Wis.) and pressed at a 1000 lb. force for 10 minutes at temperature 5° C. below the melting temperature of the PHB-O. The resulting nonwoven sheet is removed from the press.

EXAMPLE 2

Compostable Adhesive

PHB-O (50:50) may be used as a hot-melt adhesive in the following manner. About 1 g of PHB-O (50:50) is placed between two polymer films, such as poly(vinyl alcohol) (PVA), or poly(3-hydroxybutyrate) (PHB) or any other PHA which has a melting temperature at least 10° C. higher than PHB-O (50:50). The films/adhesive assembly is placed in a Carver Press (Fred S. Carver Inc., Menomonee Falls, Wis.) and is then pressed at a temperature 5° C. above the melt temperature of PHB-O (50:50). After compression at 2000 lb. force for 30 min., the pressure is released and the bonded film assembly is allowed to cool to room temperature.

EXAMPLE 3

A. Dispersion of PHA Binder

A solution made of 50 g of 92:8 poly(3-hydroxybutyrate-co-hydroxyoctanoate) copolymer dissolved in 450 g of an organic solvent such as chloroform is emulsified in 2 liters of water with the aid of sonicator. An emulsifier, e.g., oleyl ethoxylate as VOLPO-20 (Croda, Inc.) can be used in the mixture to stabilize the emulsion. The organic solvent is subsequently evaporated from the emulsion to obtain a dispersion of the copolymer binder.

B. Nonwovens Made by Dip Coating of PHA Binder 2.62 g (2.5 g dry wt.) unrefined Northern Softwood Kraft (NSK) pulp is dispersed in 500 ml tap water at ambient pH (ca. 7.5). The handsheet is made on a standard Deckle Box using tap water at ambient pH (ca. 7.5) and dried on a drum drier at 115° C. The handsheet is then immersed in the dispersion of PHA binder as described above and dried again to produce a nonwoven sheet.

EXAMPLE 4

Compostable Nonwoven Fabric

Using the PHB-O of Example 1 and the hot melt adhesive of Example 2, a compostable nonwoven fabric is prepared by placing the fibers collected on a cardboard mat with the adhesive into a Carver Press as in Example 1, thus forming a nonwoven wherein the fiber and the binder is of PHA.

EXAMPLE 5

A. Dispersion of Cationic PHA Binder

A solution made of 50 g of 98:2 poly(3-hydroxybutyrate-co-hydroxyoctadecanoate) copolymer dissolved in 450 g of an organic solvent such as chloroform is emulsified in 2 liters of water with the aid of sonicator. An emulsifier, e.g., oleyl ethoxylate as VOLPO-20 can be used in the mixture to stabilize the emulsion. To the emulsion 1.0 g of a cationic emulsifier, e.g. oleyl ethoxylate end-capped with a quaternary ammonium moiety as described in patents granted to Noda et al. (U.S. Pat. Nos. 4,835,211, issued May 30, 1989, and 4,785,030, issued Nov. 15, 1988) is added. The organic solvent is subsequently evaporated from the emulsion to obtain a cationic dispersion of the copolymer binder.

B. Nonwoven Fabrics Made by Wet-End Deposition of PHA Binder 2.62 g (2.5 g dry wt.) unrefined Northern Softwood Kraft (NSK) pulp is dispersed in 500 ml tap water at ambient pH (ca. 7.5). 1.0 g of cationic binder dispersion described in A is added to the pulp slurry and stirred for 30 minutes to promote the deposition. The handsheet is made on a standard Deckle Box using tap water at ambient pH (ca. 7.5) and dried on a drum drier at 115° C.

EXAMPLE 6

A. Dispersion of Cationic PHA Binder

A solution made of 50 g of 90:10 poly(3-hydroxybutyrate-co-hydroxyhexanoate) copolymer dissolved in 450 g of an organic solvent such as chloroform is emulsified in 2 liters of water with the aid of sonicator. An emulsifier, e.g., oleyl ethoxylate as VOLPO-20 can be used in the mixture to stabilize the emulsion. To the emulsion 1.0 g of a cationic emulsifier, e.g. oleyl ethoxylate end-capped with a quaternary ammonium moiety as described in patents granted to Noda et al. (U.S. Pat. Nos. 4,835,211, issued May 30, 1989, and 4,785,030, issued Nov. 15, 1988) is added. The organic solvent is subsequently evaporated from the emulsion to obtain a cationic dispersion of the copolymer binder.

B. Nonwoven Fabrics Made by Wet-End Deposition of PHA Binder 2.62 g (2.5 g dry wt.) unrefined Northern Softwood Kraft (NSK) pulp is dispersed in 500 ml tap water at ambient pH (ca. 7.5). 1.0 g of cationic binder dispersion described in A is added to the pulp slurry and stirred for 30 minutes to promote the deposition. The handsheet is made on a standard Deckle Box using tap water at ambient pH (ca. 7.5) and dried on a drum drier at 115° C.

EXAMPLE 7

A. Dispersion of Cationic PHA Binder

A solution made of 50 g of 92:8 poly(3-hydroxybutyrate-co-hydroxyoctanoate) copolymer dissolved in 450 g of an organic solvent such as chloroform is emulsified in 2 liters of water with the aid of sonicator. An emulsifier, e.g., oleyl ethoxylate as VOLPO-20 can be used in the mixture to stabilize the emulsion. To the emulsion 1.0 g of a cationic emulsifier, e.g. oleyl ethoxylate end-capped with a quaternary ammonium moiety as described in patents granted to Noda et al. (U.S. Pat. Nos. 4,835,211, issued May 30, 1989, and 4,785,030, issued Nov. 15, 1988) is added. The organic solvent is subsequently evaporated from the emulsion to obtain a cationic dispersion of the copolymer binder.

B. Nonwovens Made by Wet-End Deposition of PHA Binder 2.62 g (2.5 g dry wt.) unrefined Northern Softwood Kraft (NSK) pulp is dispersed in 500 ml tap water at ambient pH (ca. 7.5). 1.0 g of cationic binder dispersion described in A is added to the pulp slurry and stirred for 30 minutes to promote the deposition. The handsheet is made on a standard Deckle Box using tap water at ambient pH (ca. 7.5) and dried on a drum drier at 115° C.

EXAMPLE 8

Continuous Production of Nonwovens with PHA Binder

The applicability of cationic dispersion of PHA as a binder for nonwovens produced by wet-end deposition process is as follows. Approximately 220 kg (dry weight) of refined northern Kraft pulp is dispersed in water at the consistency of about 2.5% and kept in a stirred holding tank. About 400 liters of cationic binder dispersion (prepared according to Example 7A) is added to the pulp to achieve the wet-end deposition of the binder.

The binder-treated pulp is then fed to a pilot-scale paper machine (equipped with normal papermaking process components, such as headbox, forming wire, and continuous dryer) at a rate of 80 L/min. The paper machine is operated at the production speed of 200 m/min.

EXAMPLE 9

Compostable Disposable Diaper

A disposable baby diaper according to this invention is prepared as follows. The dimensions listed are for a diaper intended for use with a child in the 6–10 kilogram size range. These dimensions can be modified proportionately for different size children, or for adult incontinence briefs, according to standard practice.

1. Backsheet: 0.020–0.038 mm film consisting of a 92:8 poly(3-hydroxybutyrate-co-hydroxyoctanoate) copolymer; width at top and bottom 33 cm; notched inwardly on both sides to a width-at-center of 28.5 cm; length 50.2 cm.

2. Topsheet: a topsheet of nonwoven fabric of Example 8; width at top and bottom 33 cm; notched inwardly on both sides to a width-at-center of 28.5 cm; length 50.2 cm.

3. Absorbent core: comprises 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE 10

Compostable Lightweight Pantiliner

A lightweight pantiliner suitable for use between menstrual periods comprises a pad (surface area 117 $cm^2$; SSK air felt 3.0 g) containing 1.0 g of absorbent gelling material particles (commercial polyacrylate; Nippon Shokubai); said pad being interposed between a porous topsheet of Example 8 according to U.S. Pat. No. 4,463,045 and a backsheet which comprises a 0.03 mm thickness 92:8 poly(3-hydroxybutyrate-co-hydroxyoctanoate) copolymer film.

EXAMPLE 11

Compostable Sanitary Napkin

A catamenial product in the form of a sanitary napkin having two flaps extending outward from its absorbent core is prepared using a pad in the manner of Example 10 (surface area 117 $cm^2$; 8.5 g SSK air felt), per the design of U.S. Pat. No. 4,687,478, Van Tillburg, Aug. 18, 1987.

EXAMPLE 12

Compostable Disposable Diaper

The diaper of Example 9 is modified by replacing the backsheet with a backsheet consisting of a 0.020 to 0.038 mm thickness film comprising a 92:8 poly(3-hydroxybutyrate-co-hydroxydecanoate) copolymer film.

EXAMPLE 13

Compostable Disposable Diaper

The diaper of Example 12 is modified by replacing the nonwoven backsheet with a backsheet made from the nonwoven of Example 4.

EXAMPLE 14

Compostable Disposable Diaper

The diaper of Example 12 is modified by replacing the nonwoven topsheet with a nonwoven porous topsheet prepared by the methods disclosed in copending U.S. patent application Ser. No. 08/203,260, incorprated herein by reference.

All publications and patent applications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. An adhesive dispersion comprising a biodegradable copolymer wherein the biodegradable copolymer comprises at least two randomly repeating monomer units wherein each randomly repeating monomer unit has the structure:

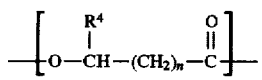

wherein $R^4$ is H, or $C_1$ to $C_{19}$ alkyl or $C_1$ to $C_{19}$ alkenyl, and n is 1 to 4.

2. The adhesive dispersion of claim 1, wherein the two randomly repeating monomer units are a first randomly repeating monomer unit having the structure:

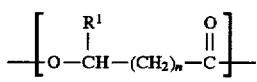

wherein $R^1$ is H, or $C_1$ to $C_{19}$ alkyl or $C_1$ to $C_{19}$ alkenyl, and n is 1 or 2; and a second randomly repeating monomer unit having the structure:

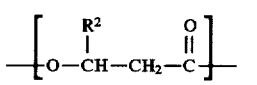

wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

3. The adhesive dispersion of claim 2, wherein $R^1$ is H, or $C_1$ or $C_2$ alkyl, and n is 1 or 2, and $R^2$ is $C_3$ to $C_{19}$ alkyl or $C_3$ to $C_{19}$ alkenyl.

4. The adhesive dispersion of claim 1, wherein the biodegradable copolymer further comprises one or more additional randomly repeating monomer units having the structure:

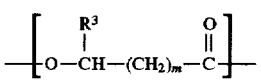

wherein $R^3$ is H, or a $C_1$–$C_{19}$ alkyl or $C_1$ to $C_{19}$ alkenyl; and m is 1 or 2; and wherein the additional randomly repeating monomer units are not the same as the first randomly repeating monomer unit or the second randomly repeating monomer unit.

5. The adhesive dispersion of claim 1, further comprising a surfactant of formula:

wherein;

X is a cationic radical chosen from the group consisting of primary, secondary or tertiary amines and their cations, and quaternary ammonium, and sulfonium and phosphonium;

Y is a nonionic diradical having up to about 20 repeating monomer units of —(OCH$_2$CH$_2$)—;

Z is an alkyl or alkenyl radical comprising of from about 8 to about 20 carbons which is branched or linear and substituted or unsubstituted.

6. A method of making a nonwoven material comprising fibers and an adhesive comprising a biodegradable copolymer, wherein the biodegradable copolymer comprises at least two randomly repeating monomer units wherein each randomly repeating monomer unit has the structure:

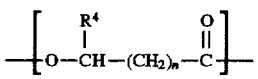

wherein $R^4$ is H, or $C_1$ to $C_{19}$ alkyl or $C_1$ to $C_{19}$ alkenyl, and n is 1 to 4 comprising the steps of a) combining the biodegradable polymer with a surfactant of formula:

wherein;

X is a cationic radical chosen from the group consisting of primary, secondary or tertiary amines and their cations, and quaternary ammonium, and sulfonium and phosphonium;

Y is a nonionic diradical having up to about 20 repeating monomer units of

Z is an alkyl or alkenyl radical comprising of from about 8 to about 20 carbons which is saturated or unsaturated, branched or linear and substituted or unsubstituted;

b) coating a fiber with a binder; and c) bonding the fibers together into a nonwoven material.

7. An adhesive dispersion comprising a biodegradable copolymer comprising the randomly repeating monomer units independently having the structure:

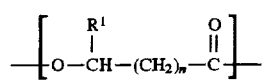
wherein n is 3 or 4 and $R^1$ is H, or a $C_1$ to $C_{19}$ alkyl or $C_1$ to $C_{19}$ alkenyl.
* * * * *